United States Patent
Logue et al.

(10) Patent No.: US 9,804,126 B2
(45) Date of Patent: Oct. 31, 2017

(54) APPARATUS AND METHOD FOR IMPROVED ACOUSTICAL TRANSFORMATION

(71) Applicant: Veeco Instruments Inc., Plainview, NY (US)

(72) Inventors: Raymond C. Logue, Henderson, NV (US); Don N. Sirota, Poughkeepsie, NY (US); William E. Quinn, Whitehouse Station, NJ (US); Owan C. Watkins, Edison, NJ (US); Maria D. Ferreira, Belle Meade, NJ (US); Wei Zhang, New Brunswick, NJ (US)

(73) Assignee: Veeco Instruments Inc., Plainview, NY (US)

( * ) Notice: Subject to any disclaimer, the term of this patent is extended or adjusted under 35 U.S.C. 154(b) by 343 days.

(21) Appl. No.: 13/705,650

(22) Filed: Dec. 5, 2012

(65) Prior Publication Data

US 2014/0060153 A1 Mar. 6, 2014

Related U.S. Application Data

(60) Provisional application No. 61/696,597, filed on Sep. 4, 2012.

(51) Int. Cl.
G01N 29/00 (2006.01)
G01N 29/036 (2006.01)
(Continued)

(52) U.S. Cl.
CPC ........... *G01N 29/00* (2013.01); *G01N 29/036* (2013.01); *G01N 29/222* (2013.01);
(Continued)

(58) Field of Classification Search
CPC ..................................................... G01N 29/00
(Continued)

(56) References Cited

U.S. PATENT DOCUMENTS 6,116,080 A * 9/2000 Logue et al. ............... 73/24.05
6,192,739 B1 2/2001 Logue et al.
(Continued)

FOREIGN PATENT DOCUMENTS

CN 1729716 A 2/2006
CN 100462694 C 2/2009
(Continued)

OTHER PUBLICATIONS

"Summary of Properties for Kapton® Polyimide Films" at http://www2.dupont.com/Kapton/en_US/assets/downloads/pdf/summaryofprop.pdf, 26 pages, as accessed on Mar. 8, 2013.
(Continued)

*Primary Examiner* — Lisa Caputo
*Assistant Examiner* — Tarun Sinha
(74) *Attorney, Agent, or Firm* — Patterson Thuente Pedersen, P.A.

(57) ABSTRACT

An acoustical transformer having a last matching section that includes a protective barrier of low permeability. The protective barrier is in contact with a test medium. In one embodiment, the protective barrier comprises one or more low permeability layers, such as a metallic foil or metallic coating(s) disposed on a low impedance layer such as polyimide, so that the low impedance layer and the protective barrier constitute the last matching section of the acoustical transformer. In other embodiments, the protective barrier comprises a fluoropolymer. A method for determining the thicknesses of the various layers of the acoustical transformer for enhanced performance is also disclosed.

27 Claims, 8 Drawing Sheets

(51) Int. Cl.
   G01N 29/22    (2006.01)
   G01N 29/24    (2006.01)
   G01N 29/28    (2006.01)
   G10K 11/02    (2006.01)

(52) U.S. Cl.
   CPC ......... *G01N 29/2437* (2013.01); *G01N 29/28* (2013.01); *G10K 11/02* (2013.01); *G01N 2291/022* (2013.01)

(58) Field of Classification Search
   USPC ................................................ 73/24.05, 649
   See application file for complete search history.

(56) References Cited

U.S. PATENT DOCUMENTS

| | | | |
|---|---|---|---|
| 6,199,423 | B1 | 3/2001 | Logue et al. |
| 6,279,379 | B1 | 8/2001 | Logue et al. |
| 2002/0124662 | A1* | 9/2002 | Suzuki et al. .............. 73/861.28 |
| 2004/0021529 | A1* | 2/2004 | Bradley ................... H03H 3/02 333/187 |
| 2005/0128030 | A1* | 6/2005 | Larson et al. ................ 333/191 |
| 2005/0236932 | A1 | 10/2005 | Nagahara et al. |
| 2006/0156828 | A1* | 7/2006 | Konzelmann et al. .... 73/861.25 |
| 2006/0198760 | A1 | 9/2006 | Potyrailo et al. |
| 2007/0170815 | A1 | 7/2007 | Unkrich |
| 2007/0205697 | A1 | 9/2007 | Chaggares et al. |

FOREIGN PATENT DOCUMENTS

| | | |
|---|---|---|
| EP | 1416255 A1 | 5/2004 |
| JP | 2001045596 A | 2/2001 |
| JP | 2003009287 A | 1/2003 |
| JP | 2003038486 A | 2/2003 |
| JP | 2006-030142 | 2/2006 |
| JP | 2006-030142 A | 2/2006 |
| JP | 2011072702 A | 4/2011 |
| KR | 10-0989896 B1 | 10/2010 |
| KR | 100989896 | 10/2010 |

OTHER PUBLICATIONS

Goldman, "Ultrasonic Technology", Reinhold Publishing Corporation, New York, 1962.

Inoue et al., "Design of Ultrasonic Transducers with Multiple Acoustic Matching Layers for Medical Applications", IEEE Transactions on Ultrasonics, Ferroelectrics, and Frequency Control, vol. UFFC-34. No. 1, Jan. 1987.

Elmore et al., "Physics of Waves", Dover Publications, Inc., New York, 1985.

Alvarez-Arenas, "Acoustic Impedance Matching of Piezoelectric Transducers to the Air", IEEE Transactions on Ultrasonics, Ferroelectrics, and Frequency Control, vol. 51, No. 5, May 2004.

Hunter, "Acoustics", Englewood Cliffs, NJ, Prentice-Hall Inc., 1957.

Maione et al., "PSpice modeling of Ultrasound Transducers: Comparison of Software Models to Experiment", IEEE Transactions on Ultrasonics, Ferroelectrics, and Frequency Control, vol. 46, No. 2, Mar. 1999.

Sherrit et al., "Comparison of the Mason and KLM Equivalent Circuits for Piezoelectric Resonators in the Thickness Mode", 1999 IEEE Ultrasonic Symposium, 0-7803-5725-6/99.

Muttakin et al., "SPICE Modeling of Hybrid Multi-Frequency Ultrasound Transducer", Recent Researches in Power Systems and Systems Science. ISBN: 978-1-61804-041-1.

International Search Report and Written Opinion for International Search Report PCT/US2013/056183 dated Jan. 14, 2014.

Singapore Application No. 11201501603Q, Written Opinion dated Nov. 12, 2015, 6 pages.

EP Application No. 13834780.2, Extended EP Search Report, dated Apr. 18, 2016, 8 pages.

Chinese Application No. 201380057166.0, First Office Action dated Jul. 20, 2016, including English translation obtained from Global Dossier, 28 pages.

Singapore Application No. 11201501603Q, Written Opinion dated Jul. 21, 2016, 6 pages.

Chinese Application No. 201380057166.0, First Office Action dated Jul. 20, 2016, 28 pages.

Baun, Chapter 8 Transducers, Physical Principles of General and Vascular Sonography, Jun. 21, 2004, pp. 93-100.

Adeyemi, DLM 14—Physics of Transducers for Imaging and Doppler, Feb. 18, 2011, Citation not enclosed due to Copyright Restrictions. A copy may be obtained at http://traktoria.org/files/sonar/transducer.

Lei Sun's Master's Thesis, Study on Fabrication of Piezoelectric Transducer with Matching Layer and Electromechanical Property Thereof (no English translation available).

Taiwan Application No. 102131583, Office Action/Search Report dated May 23, 2017, 1 page.

Japanese Office Action for Application No. 2015-529873, 8 pages.

* cited by examiner

APPARATUS AND METHOD FOR IMPROVED ACOUSTICAL TRANSFORMATION

RELATED APPLICATIONS

This application claims the benefit of U.S. Provisional Patent Application No. 61/696,597 entitled "Apparatus and Method for Improved Acoustical Transformation," filed Sep. 4, 2012, the disclosure of which is hereby incorporated by reference herein in its entirety.

FIELD OF THE INVENTION

The disclosure is directed generally to acoustical measurements performed on gases, liquids or solids, and more specifically to acoustical transformers utilized in acoustical measurements.

BACKGROUND

Numerous industries employ processes that require accurate delivery of gas mixtures comprising a gas of interest dispersed within a carrier gas. Accurate delivery of such gas mixtures requires precise measurements of the concentration of the gas of interest in the flowing gas mixture, where the gas of interest is typically of high purity and may be highly corrosive. Examples of these processes include chemical vapor deposition (CVD), dopant diffusion (e.g., as practiced in the semiconductor industry), and operation of high efficiency hydrogen cooled generators.

One method of controlling the flux of the gas of interest or reactant is the use of a carrier gas, typically hydrogen or nitrogen, which is flowed through a vaporizer or "bubbler". The flow of carrier gas is controlled by a mass flow controller, and the concentration of reactant in the gas stream as it exits the vaporizer is assumed to be constant, and the flux of the reactant is proportional to the flow of carrier gas. This approach is inaccurate for several reasons, including, variations in the bubbler temperature, instability of the temperature and pressure of the binary gas mixture, possible leakages in the gas lines upstream and downstream of the bubbler, and concentration time delays between the mass flow controllers and the points of interest, especially at low flow rates.

U.S. Pat. Nos. 6,116,080, 6,192,739, 6,199,423 and 6,279,379, commonly owned by the owner of this patent application, discloses a technique and device that is an improvement over the pre-mixing measurements. These patents disclose an acoustical measuring device that infers the concentration of a gas of interest downstream of the bubbler and after the vaporization process, herein referred to as a "post-mixing measurement."

Certain aspects of these patents and the post-mixing measurement technique are embodied in the PIEZOCON Concentration Sensor (hereinafter "Piezocon Sensor"), manufactured and sold by Veeco Flow Technologies, Inc. of Poughkeepsie, N.Y., USA. The Piezocon Sensor utilizes an acoustical transformer comprising a low impedance interface. Herein, an "acoustical transformer" is defined as a layer or multi-layer interface between an acoustical element (sensor or driver) such as a piezoelement and the medium under measurement. Desirable characteristics of acoustical transformers include high efficiency over a broad band of acoustical frequencies, matching of the low acoustical impedance of the test medium and an exposed surface having resistance to chemical reaction with the test medium.

Polyimides, such as Kapton® film, are a preferred material for acoustical transformers because polyimides provide a low impedance matching layer having resistance to chemical reaction comparable to other materials traditionally used in acoustical transformers such as fluoropolymers while providing a more stable Young's Modulus across the temperatures of interest.

However, despite the reasonably high chemical resistance of polyimides, it has been discovered that, over time in a metal-organic chemical vapor deposition (MOCVD) system utilizing indium-gallium-nitride, the polyimide components of the acoustical transformers become coated with gallium and indium oxides, the accrual of which is believed to cause drift in the sensor due to reducing distance between the transducers and affecting the transfer function of the acoustical transformer. Polyimides are also known to swell due to absorption of the chemicals, which can also reduce the distance between the transducers and affect the transfer function.

There is a need, therefore, for an acoustical transformer for use in post-mixing measurements that possess the favorable mechanical attributes of polyimide while mitigating the attendant chemical reactions that occur in certain post-mixing measurement environments.

SUMMARY

In various embodiments of the invention, acoustical transformers formed of materials having favorable mechanical characteristics but prone to chemical reaction in certain applications are conditioned by including a thin protective layer as a part of the last matching section of an acoustical transformer. This thin layer is made out of a low permeability material, such as metal, on the exposed face of the modified last matching section of the acoustical transformer (i.e., at the interface of the acoustical transformer and the medium under test). Such an approach is counter to conventional wisdom that the exposed face at the interface must be of a material that provides a better matching of acoustical impedance than metals provide.

In another embodiment of the invention, a low permeable polymer, such as a fluoropolymer, is utilized, solely as a way to reduce permeation of gases into the high permeability layer beneath, and despite providing unfavorable mechanical characteristics.

Research for the current work has found that the exposure of polymers that make up an acoustical transformer to very aggressive precursors has deleterious effect due to the permeation of the gases or sometimes liquids into the structure of these polymers. Chemicals can become trapped within the polymer and, even though these chemicals may possess a low reactivity with the polymer, their entrapment exacerbates the problem of chemical reaction. Polyimide films have favorable mechanical characteristics (i.e., relatively stable modulus of elasticity) as well as have a reasonably high resistance to chemical reaction, but are permeable to many gases. Examples of other polyimide films include APICAL, KAPTREX, NORTON TH, UPILEX and VTEC PI. Other polymer films besides polyimide films can be utilized, including but not limited to polyamides, fluoropolymers and polyethylene.

For example, a polyimide KAPTON type FIN film of 25 µm thickness has a permeability on the order of 7000 mL/m$^2$·24 h·MPa for carbon dioxide, on the order of 4000 mL/m$^2$·24 h·MPa for oxygen, on the order of 1000 mL/m$^2$·24 h·MPa for nitrogen, on the order of 38,000 mL/m$^2$·24 h·MPa for hydrogen and on the order of 63,000 mL/m²·24 h·MPa for helium. If the permeability of the last matching section of the acoustical transformer were reduced to, for example, approximately 10% of the permeability of KAPTON for a given gas, the deleterious effects of permeability would be substantially reduced. See "Summary of Properties for Kapton® Polyimide Films[.pdf]," available at http://www2.dupont.com/Kapton/en_US/assets/downloads/pdf/summaryofprop.pdf (last visited 24 Aug. 2012). The test method for determining the permeability parameters reported therein is ASTM D-1434-82 (1988).

If the exposed face of the last matching section of an acoustical transformer has a permeability that is substantially reduced (e.g., to approximately 10% or less) the permeability of polyimide KAPTON type HN film of 25 μm thickness, the longevity of the acoustical transformer will be satisfactory for many applications. Accordingly, using the permeability of carbon dioxide as a benchmark, a material that has a carbon dioxide permeability of less than 700 mL/m²·24 h·MPa over a hypothetical thickness of 25 μm is of sufficiently low permeability to improve the durability of the acoustical transformer.

One issue is how to prevent permeation of the polymers that comprise an acoustical transformer. A limiting aspect in the application of acoustical transformers is that there can be a substantial mismatch of the acoustical impedances, particularly with the test medium is a gas, leading to the reflection of the acoustical energy at the interface which causes inefficient sensing of acoustical energy. Consider a plane acoustical wave and normal incidence at the boundary of two semi finite media. The amplitude reflection coefficient R is expressed by $$R = \frac{z_2 - z_1}{z_2 + z_1} \quad \text{Eq. (1)}$$

where $Z_1 = \rho_1 C_1$ and $Z_2 = \rho_2 C_2$ are the acoustical impedances of the first and second media, respectively, ρ is the respective density and C is the speed of sound in the respective media. By way of non-limiting example, consider a system having a transmitter where the first or propagating medium is stainless steel 316L and the second or receiving medium is nitrogen. Stainless steel 316L (commonly accepted for use in the semiconductor industry) has an acoustical impedance on the order of 45×10⁶ Pa·s/m, while nitrogen gas has an acoustical impedance on the order of 400 Pa·s/m at room temperature. In this example, the reflectivity R approaches unity, i.e., almost all acoustical energy at the stainless steel/nitrogen gas interface is reflected.

Now consider a receiver complementary to the transmitter, where the propagating and receiving media are reversed. That is, the propagating medium is the gas, and the receiving medium is stainless steel 316L. The magnitude of the reflectance is similar, but with the opposite phase. The high reflection coefficient between the two interfaces makes the acoustical signals received by the receiver undetectable.

Accordingly, it is common industry practice to utilize a multilayer acoustical transformer to improve the acoustical matching of materials having the substantially different acoustical impedances. Generally, low-impedance layers are made out of polymers (e.g., TEFLON), which are used in combination with the stainless steel layers inside the sensors. However, in certain applications, all the polymers are permeable to the gases (and in some instances the liquids) of the medium under test. When aggressive precursors become trapped in the polymers, the gases may react with the precursors and this leads to the chemical reaction causing the accumulation of the build-up of the oxides on the polymer surfaces or even inside the polymer layers. This accumulation leads to the reduction of the distance between the transmitting and receiving transducers and also to the distortion of the transfer function of the acoustical signal. Thus, conventional wisdom is that an additional matching layer of a metal (e.g., stainless steel) will create a severe mismatch and, in turn, undetectable signals.

Some embodiments of this invention are contra to this conventional wisdom. In these embodiments a thin layer of a metal or other low permeability solid, such as stainless steel 316L or INCONEL 600, covers or is otherwise added to the polymer, the low permeability solid having a thickness that is not greater than 0.05λ, and preferably less than 0.01λ. Herein, λ is referred to as the "wavelength of the acoustical wave," and is given as $$\lambda = C/f_C \quad \text{Eq. (2)}$$

where C is the speed of sound in the material of the low permeability solid and $f_C$ is the center operating frequency of the transducer. A solution for the thicknesses of the low impedance layer can be obtained using a simulation such that the resonance frequencies of the highest and lowest resonance frequencies of the low impedance layer/protective barrier combination are within a predetermined frequency range. In one embodiment, the predetermined frequency range falls between $0.75 \cdot f_C$ and $1.25 \cdot f_C$.

Commonly used polymers for the matching layers of the acoustical transformers include fluoropolymers, such as Perfluoroalkoxy (PFA), fluorinated ethylene propylene (FEP) and polytetrafluoroethylene (PTFE). Fluoropolymers have reasonably low permeation rate, however they cannot be used in a wide temperature range because of the substantial variations of the modulus of elasticity with temperature leading to the large variations of the transfer function.

One of the best candidates for the low acoustical impedance material of the acoustical transformer is polyimide (e.g., KAPTON), which can be used at the temperatures up to 400° C. and has substantially stable modulus of elasticity relative to fluoropolymers. While polyimide is chemically resistant to most of the chemicals, the higher permeation rate of polyimide for the gases and liquids amplifies the problem of the chemical reaction with the trapped gases or liquids.

Structurally, an apparatus for acoustically determining a property of a test medium is described, comprising a chamber for containment of a test medium, the chamber having at least a first side and an inlet for the test medium. A first acoustical transformer is operatively coupled with the first side of the chamber and configured to either transmit a pulse of acoustical energy into the test medium, receive a pulse of acoustical energy transmitted through the test medium, or both transmit a pulse of acoustical energy into the test medium and receive a pulse of acoustical energy transmitted through the test medium. An acoustical element, such as an acoustical driver/transmitter or an acoustical sensor/receiver, can be operatively coupled with the first acoustical transformer. The first acoustical transformer includes: a base matching section, a first surface of the base matching section being in contact with the acoustical element; and a last matching section operatively coupled with the base matching section, the last matching section including a protective barrier disposed on a low impedance layer.

It is noted that conventional terminology in the art of acoustical transformers refers to a "first" section or "first" matching layer as the layer in contact with the acoustical element (sensor or driver) of a receiver or transmitter.

Herein, the lexicon of a "base" matching section is adopted as an equivalent to "first" matching layer. It is further noted that a "matching section" (e.g., base matching section or last matching section) can include one or more layers, and that there can be additional matching sections disposed between the base and last matching sections.

In one embodiment, the low impedance layer of the first acoustical transformer is in contact with a second surface of the base matching section, the second surface of the base matching section being opposite the first surface of the base matching section, the protective barrier having an exposed face adapted for contact with the test medium.

In one embodiment, the acoustical element is an acoustical transmitter and the first acoustical transformer is configured to transmit the pulse of acoustical energy into the test medium. Also, a second acoustical transformer can be operatively coupled with a second side of the chamber and configured receive a transmitted pulse of acoustical energy transmitted through the test medium, and an acoustical sensor operatively coupled with the second acoustical transformer. The second acoustical transformer can include: a base matching section having a first surface in contact with the acoustical sensor; a last matching section operatively coupled with the base matching section of the second acoustical transformer and including a protective barrier disposed on a low impedance layer. In one embodiment, the low impedance layer of the second acoustical transformer is disposed on a second surface of the base matching section of the second acoustical transformer. In one embodiment, the second surface of the base matching section of the second acoustical transformer can be opposite the first surface of the base matching section of the second acoustical transformer. Also, the protective barrier of the second acoustical transformer can have an exposed face adapted for contact with the test medium.

In various embodiments, acoustical receiver is disposed on a second side of the chamber, and the second side of the chamber is parallel to the first side of the chamber. The acoustical elements can be constructed of a piezoceramic material. The protective barriers can comprise a metal or metal alloy, and in certain embodiments the metal of the protective barriers is a composite of a plurality of successive metal layers. Alternatively, the protective barrier can comprise a fluoropolymer, and oxide or a ceramic. Also in various embodiments, the low impedance layer of a given acoustical transformer comprises a polyimide. In still other embodiments, the acoustical element is bi-directional and configured to both transmit acoustical energy and receive acoustical energy. In one embodiment, the protective barrier comprises a material that has a carbon dioxide permeability that is less than 700 mL/m$^2$·24 h·MPa over a hypothetical thickness of 25 μm.

In other embodiments, the low impedance layer of a given acoustical transformer has a modulus of elasticity that varies less than 50% over a range from 0° C. to 400° C., and the protective barrier comprises a low permeability fluoropolymer.

In certain embodiments, a method for protecting a last matching section of an acoustical transformer is utilized. The method includes:
  establishing a predetermined thickness of a protective barrier of a last matching section of an acoustical transformer, the protective barrier being of a low permeability material for exposure to a test medium;
  determining a thickness of a base matching section of the acoustical transformer for operative coupling with the last matching section of the acoustical transformer;
  determining a thickness of a low impedance layer of the last matching section of the acoustical transformer for contact with the protective barrier, the thickness of the low impedance layer being selected to theoretically provide the acoustical transformer with resonance frequencies that fall within a predetermined frequency range.

The method can further comprise constructing the acoustical transformer having the base matching section and the last matching section, the protective barrier having the predetermined thickness, the low impedance layer having the thickness of the low impedance layer, and the base matching section having the thickness of the base matching section. In one embodiment, the method includes placing the base matching section in direct physical contact with the last matching section of the acoustical transformer.

In one embodiment, the acoustical transformer is designed as a transmitting acoustical transformer. In this embodiment, a method for designing a receiving acoustical transformer can be designed as well, the method further comprising:
  establishing a predetermined thickness of a protective barrier of a last matching section of a receiving acoustical transformer, the protective barrier of the receiving acoustical transformer being of a low permeability material for exposure to the test medium;
  determining a thickness of a base matching section of the receiving acoustical transformer for operative coupling with the last matching section of the acoustical transformer; and
  determining a thickness of a low impedance layer of the last matching section of the receiving acoustical transformer for contact with the protective barrier of the receiving acoustical transformer.

In this method, the thicknesses of the low impedance layer of the transmitting acoustical transformer and the low impedance layer of the receiving acoustical transformer can be selected to theoretically provide both the transmitting acoustical transformer and the receiving acoustical transformers with resonance frequencies that fall within a predetermined frequency range.

In one embodiment, a metallic protective barrier is implemented by bonding a metallic foil to the low impedance layer. In other embodiments, the step of disposing a metallic protective barrier includes a chemical vapor deposition process and/or successively disposing a plurality of different metals onto the low impedance layer.

DETAILED DESCRIPTION

Figure 1:
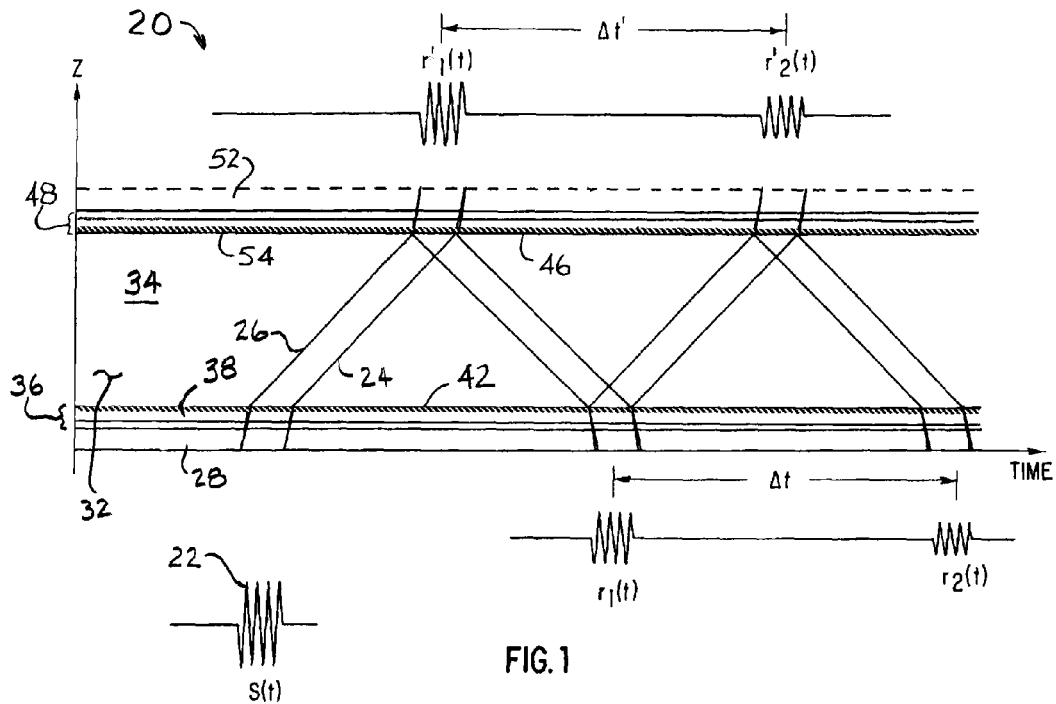
FIG. 1 is an acoustic cell timing diagram in an embodiment of the invention.

Referring to FIG. 1, an acoustic cell timing diagram 20 is depicted in an embodiment of the invention. A pulse of acoustical energy 22 having a leading edge 24 and a trailing edge 26 in time is emitted by a transducer 28 and coupled into a test chamber 32 containing a test medium 34 by a first acoustical transformer 36 having a low impedance layer 38 coupled with a protective barrier 42. The first acoustical transformer 36 can be tailored to provide efficient energy transfer between the transducer 28 and the test medium 34. The pulse of acoustical energy 22 produced in this way constitutes the transmitted signal S(t). The pulse of acoustical energy 22 traverses the test chamber 32 through the test medium 34 and is incident on an opposing surface 46 of the test chamber 32. A time trace showing signals $r'_1(t)$ and $r'_2(t)$ received by the opposing surface 46 and separated by a time interval $\Delta t'$ is depicted in FIG. 1.

In one embodiment, herein referred to as an "echo configuration," the opposing surface 46 is a high efficiency reflector (not depicted), characterized by a reflection coefficient that approaches unity. The objective of the high efficiency reflector of the echo configuration is to reflect the acoustical energy back to the first acoustical transformer 36 for detection. A time trace showing signals $r_1(t)$ and $r_2(t)$ reflected back to the first acoustical transformer 36 separated by a time interval $\Delta t$ is also depicted in FIG. 1. In one embodiment, emitting transducer 28 can be bi-directional (i.e., suitable for both generating and detecting acoustical energy) for this purpose.

In another embodiment, herein referred to as a "shadow configuration," the opposing surface 46 of the test chamber includes a second acoustical transformer 48, coupled with a receiving transducer 52 on one face and having a protective barrier 54 on the opposite face. The second acoustical transformer 48 can be tailored for a low reflection coefficient. A "low reflection coefficient" is a reflection coefficient that substantially improves the strength of the detected signal in comparison to a system that has no matching acoustical transformer. For a continuous wave and for solid state or liquid media, a low reflection coefficient is one that is close to zero. For a gas/solid interface, however, the reflection coefficient computed by Eq. (1) can be close to unity—on the order of 0.9999 and greater—because the acoustical impedance of a solid (on the order of $10^6$ Pa·s/m) is much greater than for a gas (on the order of a few hundred Pa·s/m). Nevertheless, the near-unity reflection coefficient can still be "low" because the signal-to-noise ratio of the received signal is several factors or even orders of magnitude greater than for a system not implementing a matching acoustical transformer.

The low reflection coefficient can provide efficient transfer between the test medium 34 and the receiving transducer 52, and can also be of similar construction as the first acoustical transformer 36. The shadow configuration is particularly suitable for applications where the test medium 34 is quite lossy at the frequency of operation and there is a substantial mismatch in the acoustical impedance between the testing medium and the acoustical transducers.

In certain embodiments, the first and second acoustical transformers 36 and 48 are not designed separately for low reflection coefficients, but rather as a system wherein the interaction between the first and second acoustical transformers 36 and 48 is considered to provide a desirable transfer function.

For high efficiency matching of acoustical impedance, conventional wisdom is that the exposed layer (layer in contact with the medium under test) of a multilayer acoustical transformer have a low acoustical impedance (low reflection coefficient pursuant to Eq. (1)) for proper acoustical matching with the test medium. However, for various embodiments of the present invention, the protective barrier 54 can be comprised of materials having a high acoustical impedance, such as metals. Research for the current work has revealed that if the second matching layer is designed as a composite structure, then the performance of the acoustical transformer is not substantially compromised by protective barriers 54 of high acoustical impedance that are sufficiently thin (i.e., protective barriers having a thickness on the order of $0.01\lambda$).

Figure 2:
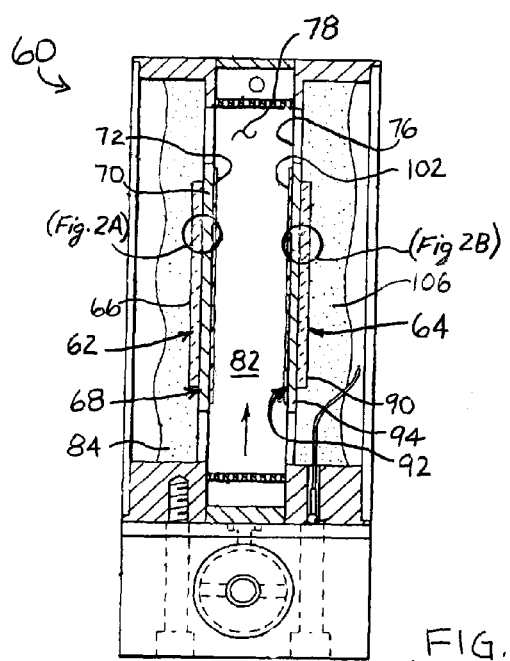
FIG. 2 is an acoustical sensor constructed in a "shadow" configuration.
Figure 2A:
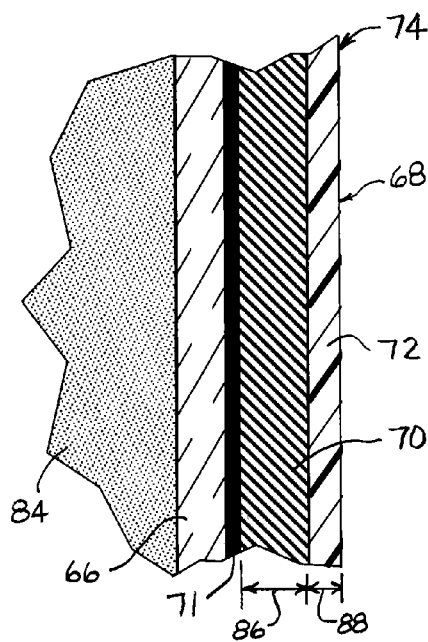
FIGS. 2A and 2B are enlarged partial sectional views of a transmitter and a receiver, respectively, of the acoustical sensor of FIG. 2.
Figure 2B:
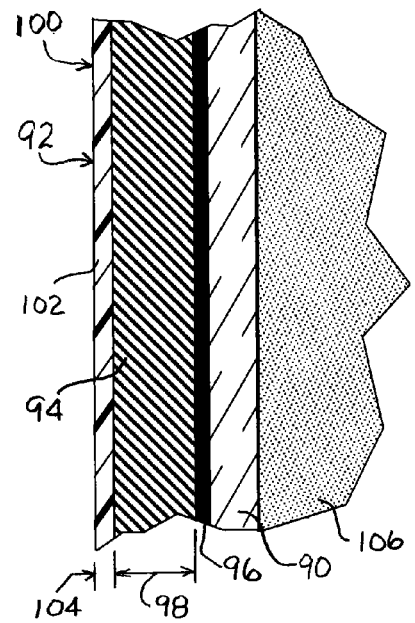

Referring to FIGS. 2, 2A and 2B, a baseline acoustical sensor 60 of the prior art and in a shadow configuration is depicted. The baseline configuration 60 includes a transmitter 62 and a receiver 64. The transmitter 62 includes an acoustical driver 66 adhered to a transmitting acoustical transformer 68, for example with a layer of glue 71. The transmitting acoustical transformer 68 comprises a first section or base matching section 70 to which is laminated a last matching section 74 of a low impedance layer 72 of a low impedance material such as polyimide. The base matching section 70 is often metallic, such as 316L stainless steel. In other embodiments, the last matching section 74 is operatively coupled with the base matching section 70, but with one or more intermediate matching sections (not depicted) disposed between the base and last matching sections 70 and 74.

The last matching section 74 defines a portion of a boundary 76 that defines a chamber 78, the chamber 78 containing a gas medium 82 under test. The backside of the acoustical driver 66 is in contact with a mechanical damper 84. The first section or base matching section 70 and the last matching section 74 are characterized as having thicknesses 86 and 88, respectively.

In the depicted embodiments, the receiver 64 includes the same material components as the transmitter 62, although the thicknesses of the components can differ from the transmitter: an acoustical sensor 90 attached to a receiving acoustical transformer 92 comprising a stainless steel base matching section 94 with a layer of glue 96, the stainless steel base matching section 94 having a thickness 98, a last matching section 100 comprising low impedance layer 102 having a thickness 104 laminated on the stainless steel base matching section 94, the polyimide being adjacent the test medium 82. The backside of the acoustical sensor 90 is in contact with a mechanical damper 106.

In one embodiment, the acoustical driver 66 and the acoustical sensor 90 comprise piezoceramic elements. In one embodiment, the mechanical damper 106 comprises tungsten powder mixed with a low viscosity epoxy, the proportions of which depend upon the specific configuration and components of the sensor. Other combinations of fine powders, such as tungsten or cement, can be mixed with, for example, epoxy or melted rubbers for the mechanical damper 106. In various embodiments, the mechanical damper 106 is designed for an acoustical impedance close to the acoustic element and very high absorption.

Figure 3:
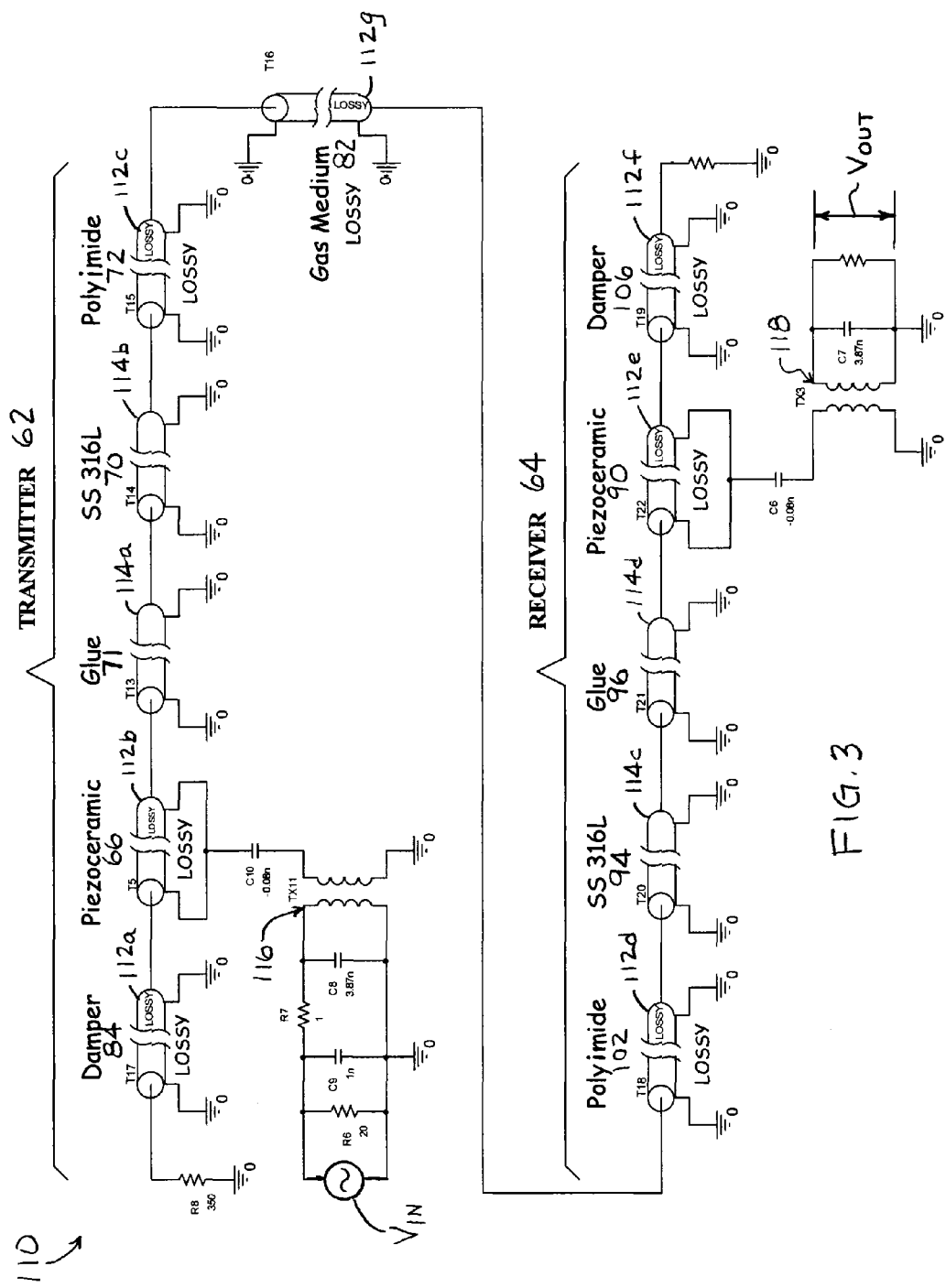
FIG. 3 is a baseline circuit model of the acoustical sensor of FIG. 2.

Referring to FIG. 3, a baseline circuit model 110 for the system of FIG. 2 is depicted. For the current work, a SPICE (Simulation Program with Integrated Circuit Emphasis) model was utilized, but other circuit models can also be implemented. In the depicted model, the acoustical elements 66 and 90, low impedance layers 72 and 102, mechanical dampers 84 and 106 and gas medium 82 are modeled as lossy transmission lines 112a-112g, while the glue layers 71 and 96 and stainless steel base matching sections 70 and 94 are modeled as simple transmission lines 114a-114d due to small attenuation of the acoustical energy in these elements.

The acoustical driver 66 and sensor 90 are presented based on the Redwood's version of the Mason's equivalent circuit with current transformers 116 and 118 for generation and detection, respectively, of the acoustical signals. In the depicted embodiment, the current transformer 116 is connected to a voltage source 118 which generates variable frequency voltage $V_{IN}$. The current transformer 118 can be reversed, transmitting a variable frequency signal output of $V_{OUT}$.

Using the baseline circuit model 110, it was found that a structure having the following characteristics achieved both high efficiency with the low impedance gases and a wide frequency bandwidth:

Transmitting acoustical transformer 68: base matching section 70 of 316L stainless steel with thickness 86 of 0.458λ and low impedance layer 72 of polyimide with thickness 88 of 0.315λ.

Receiving acoustical transformer 92: base matching section 94 of 316L stainless steel with thickness 98 of 0.5516λ and low impedance layer 102 of polyimide with thickness 104 of 0.21λ.

Figure 4:
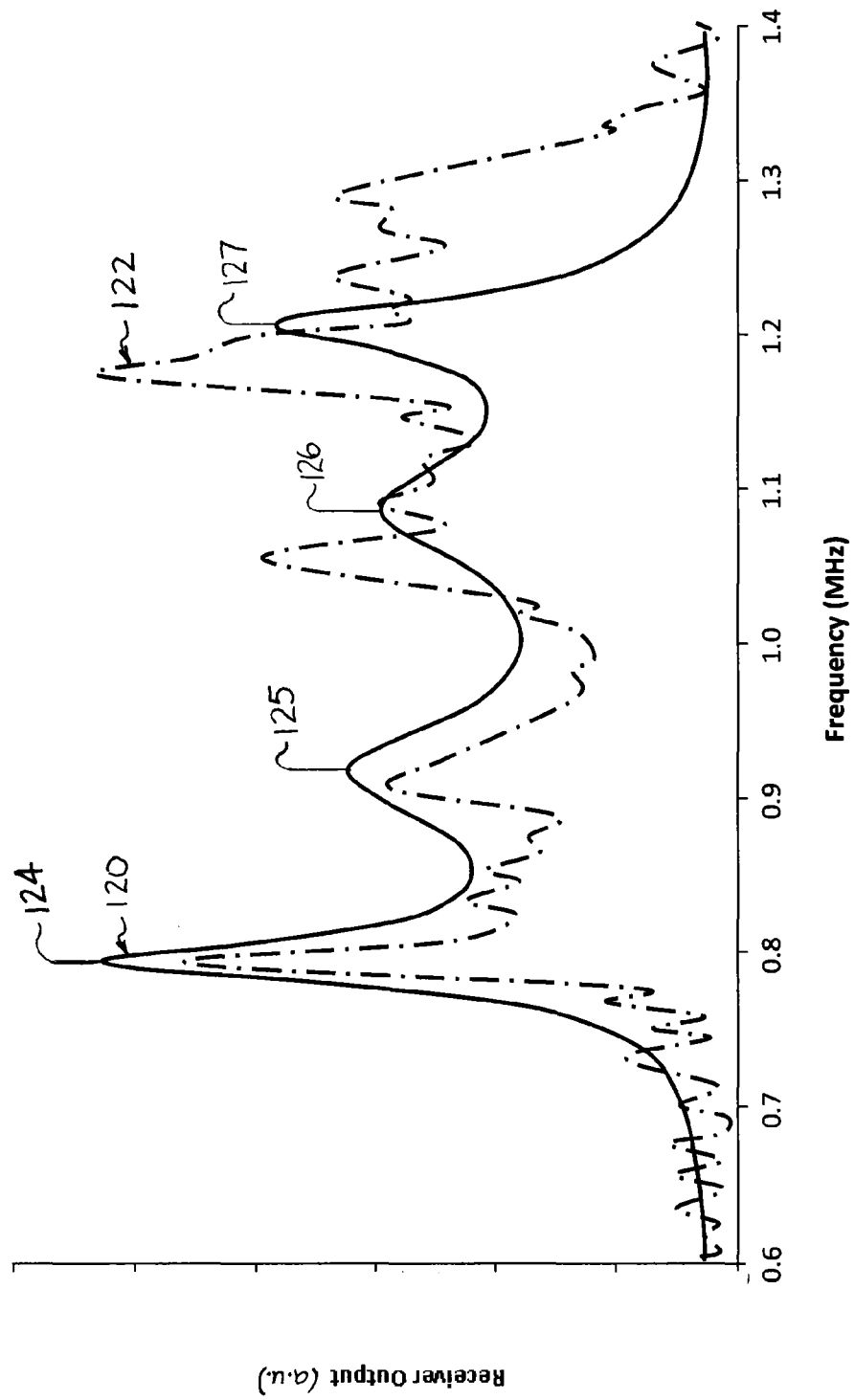
FIG. 4 is a predicted baseline transfer function calculated using the circuit model of FIG. 3 and experimental results.

Referring to FIG. 4, a predicted baseline transfer function 120 calculated by the circuit model 110 of FIG. 3 is depicted. The baseline circuit model 110 was simulated for the input voltage $V_{IN}$ of 10 volts in the bandwidth of 0.6-1.4 MHz for a transducer centered at 1 MHz. An actual baseline transfer function 122 is also presented in FIG. 4, obtained from an implementation similar to the above-described baseline configuration and utilizing piezoceramic drivers and sensors having center frequencies of 1.0 MHz. The actual baseline transfer function 122 is in substantial agreement with the predicted baseline transfer function 120. The output (ordinate) of the graph in FIG. 4 is presented in arbitrary units.

The predicted baseline transfer function 120 includes a first resonance frequency 124 located near 0.8 MHz that is primarily influenced by the resonance frequency of the last matching section 74 of the transmitting acoustical transformer 68. A second resonance frequency 125, located near 0.92 MHz, is primarily influenced by the resonance frequency of the base matching section 94 of the receiving acoustical transformer 92. A third resonance frequency 126 (near 1.08 MHz) is primarily influenced by the resonance frequency of the base matching section 70 of the transmitting acoustical transformer 68. A fourth resonance frequency 127 (near 1.2 MHz) is primarily influenced by the resonance frequency of the last matching section 100 of the receiving acoustical transformer 92. Changes to one of the matching sections 70, 74, 94 or 100 can also have a secondary or lesser effect on the location of the resonance frequencies as well. That is, a change to the base matching section 94 can have a minor effect on the location of the resonance frequencies 124, 126 and/or 127 in addition to a major effect on the location of the resonance frequency 125; a change to the base matching section 70 can have a minor effect on the location of resonance frequencies 124, 125 and/or 127 in addition to a major effect on the location of the first resonance frequency 126; and so on.

Figure 5A:
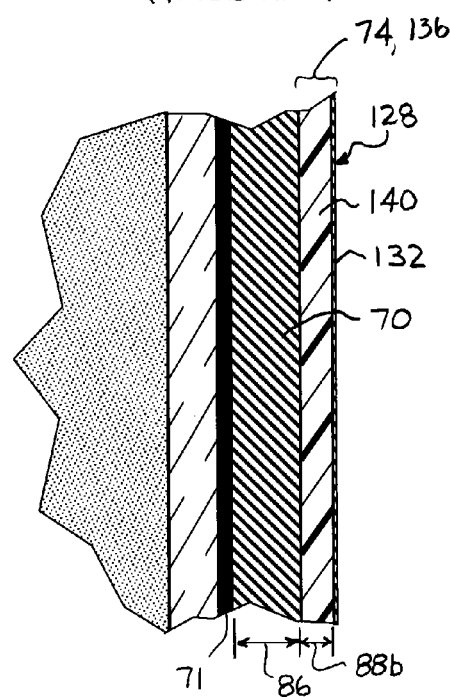
FIGS. 5A and 5B are enlarged partial sectional views of a transmitter and a receiver, respectively, having modified acoustical transformers in an embodiment of the invention.
Figure 5B:
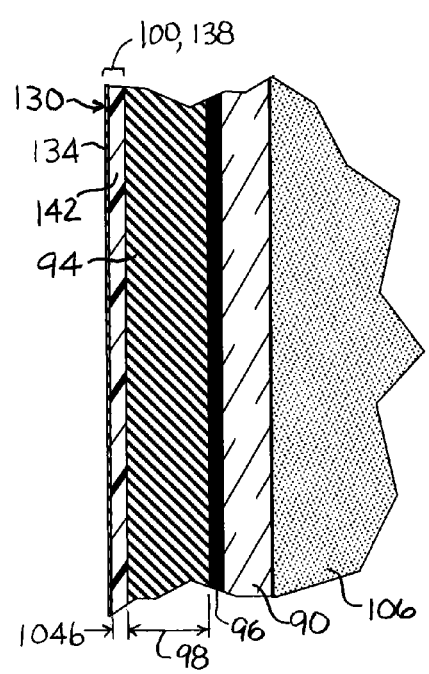

Referring to FIGS. 5A and 5B, modified acoustical transformers 128 and 130 are depicted in an embodiment of the invention. The modified acoustical transformers 128 and 130 each include the same base matching sections 70 and 94 of the acoustical transformers 68 and 92. The last matching sections 74, however, comprise complex matching layers 136 and 138, respectively. The complex matching layers 136 and 138 can include a combination of low impedance layers 140 and 142 with thin layers of a low permeability protective solid 132 and 134. The protective barriers 132 and 134 are characterized as being a material or composite of materials that provides high chemical resistance and a low permeability to the test medium 82, to protect the low impedance layers 140 and 142 from substantial contact with the test medium 82.

In one embodiment, the protective barrier(s) 132 and/or 134 comprises a metallic foil laminated to the low impedance layer(s) 72 and/or 102. Candidate materials for the metallic foils for various applications include essentially any metal that is compatible with or resistant to chemical attack from the test medium, e.g., stainless steel 316L, INCONEL, aluminum/aluminum alloys, copper/copper alloys, nickel/nickel alloys.

In another embodiment, the protective barrier(s) 132 and/or 134 comprises one or more metallic or oxide films deposited on the low impedance layer(s) 140 and 142, for example by a vapor deposition process. For example, gold is compatible with almost all chemicals that would be utilized in a MOCVD process, and provides low permeability. However there are practical difficulties of depositing gold directly on polyimide. Thus, to implement a gold layer in contact with the test medium 82, one solution is to first coat the low impedance layer(s) 140 and 142 with copper, which provides good adherence to polyimide, then to coat the copper with nickel, which adheres well to both copper and gold, then finish with the gold layer. Accordingly, providing durable bonding between the exposed metal film and the low impedance layer is, in some instances, best achieved by an additional low impedance layer or layers between the exposed metal film and the low impedance layer. Other metal film combinations include any suitable metal that can bond with the copper and possesses the necessary resistance characteristics for compatibility with the test medium, such as nickel/nickel alloys, MONEL alloys, HASTELLOY alloys and INCONEL alloys. Other metals are also suitable for direct bonding to the low impedance layer, for example nickel and nickel alloys.

In other embodiments, the protective barrier(s) 132 and/or 134 comprises a fluoropolymer, such as PFA, FEP or PTFE, deposited on the low impedance layer(s) 140 and 142. Still other embodiments include protective barrier(s) 132 and/or 134 of oxides or ceramics, for example, silica, alumina, boron nitride, synthetic diamond or diamond-like carbon (DLC) that can be applied, for example, by a sputtering process. These alternative coatings can provide resistance to chemical attack and an adequately low permeability, while the low impedance layer(s) 140 and 142 provides desirable mechanical characteristics for an acoustical transformer, such as an adequately stable modulus of elasticity across a broad temperature range (e.g., up to temperatures of 400° C.).

Figure 6:
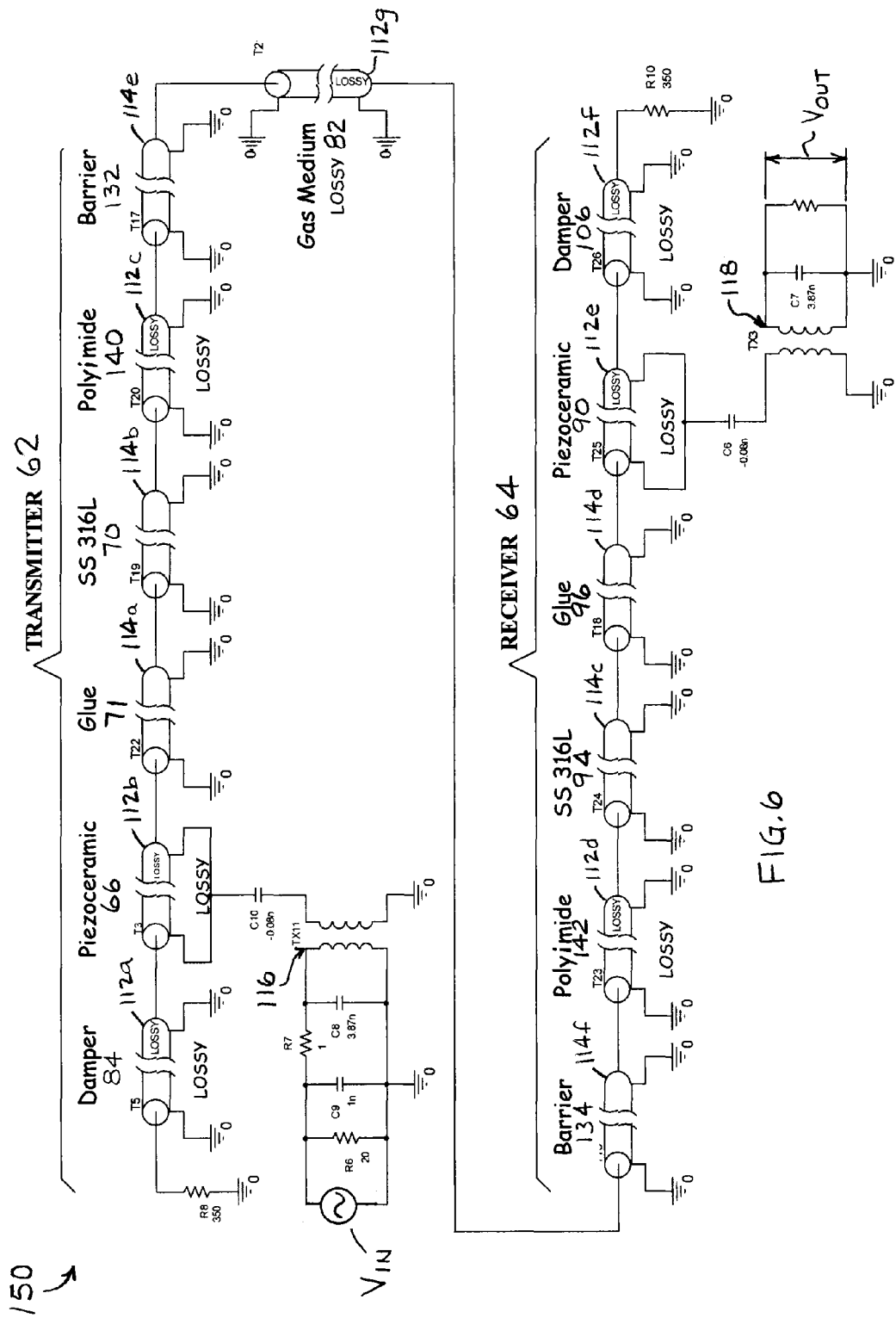
FIG. 6 is a modified circuit model of an acoustical sensor including a protective barrier in an embodiment of the invention.

Referring to FIG. 6, a modified circuit model 150 is depicted in an embodiment of the invention. The modified circuit model 150 includes the same aspects as the baseline circuit model 110 (depicted with like numerical references). It is noted that transmission lines 112c and 112d of FIG. 6 are modified to reflect the properties of the low impedance layers 140 and 142. The barriers 132 and 134 are modeled by the addition of transmission lines 114e and 114f for the protective barriers 132 and 134, respectively, between the polyimide lossy transmission lines 112c, 112d and the gas medium lossy transmission line 112g. The protective barrier transmission lines 114e and 114f, though depicted as a single transmission lines, can comprise several transmission lines in serial, depending on the construction of the protective barrier being modeled. For example, for a single foil material laminated to a polyimide layer, the protective barrier transmission line can be modeled as a single transmission line having the characteristics of the foil material. In other instances, where a composite of successive thin metal films deposited on the polyimide layer, each of those films is modeled as its own transmission line in series with the others.

Figure 7:
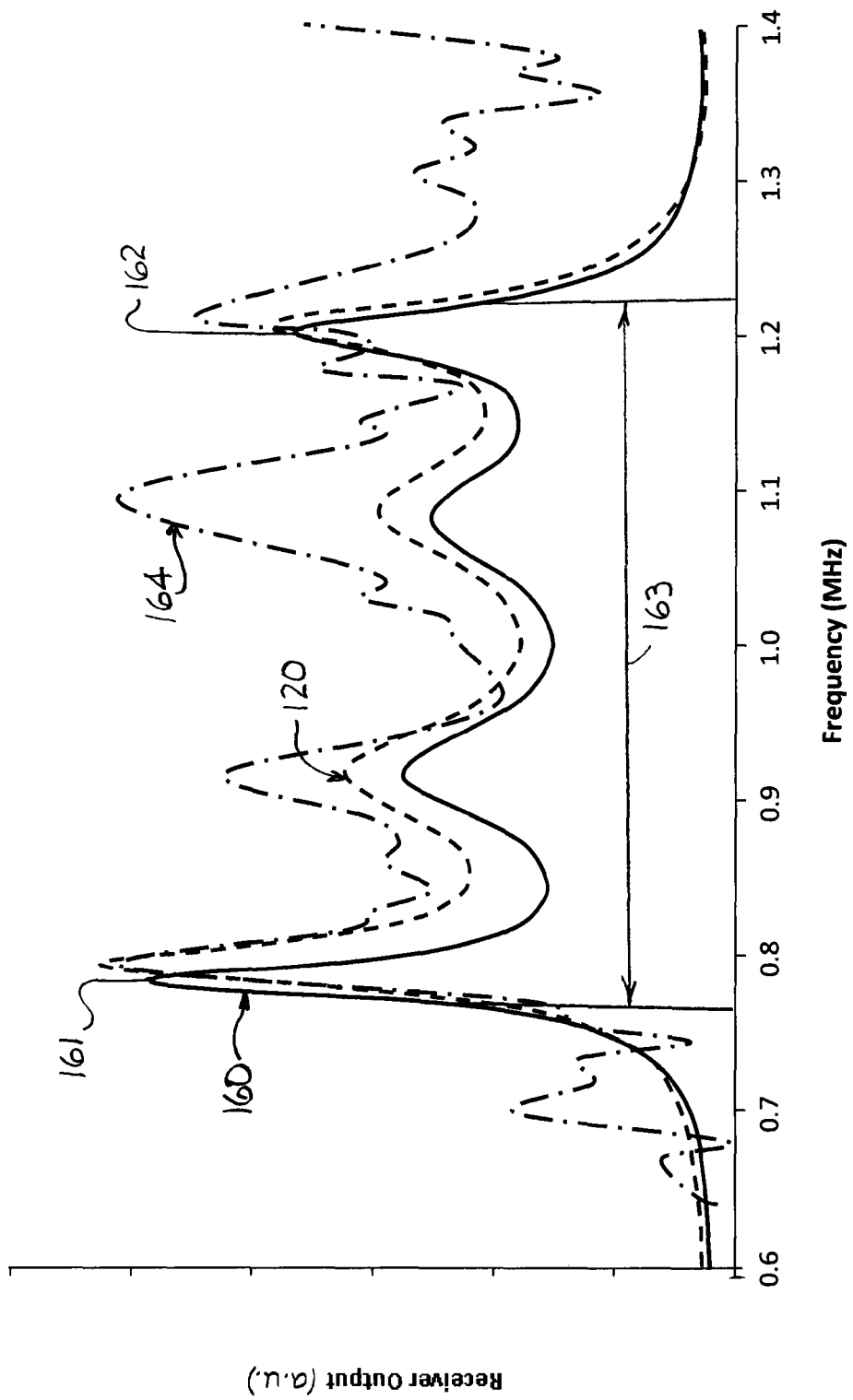
FIG. 7 is a comparison of the predicted baseline transfer function with a predicted first modified transfer function of the modified circuit model of FIG. 6 and experimental results for a protective barrier of stainless steel 316L foil bonded to a low impedance layer in an embodiment of the invention.

Referring to FIG. 7, a first predicted modified transfer function 160 from the modified circuit model 150 is compared with the predicted baseline transfer function 120 in an embodiment of the invention. To obtain the first predicted modified transfer function 160, the protective barrier transmission lines 114e and 114f of the modified circuit model were modeled as a single layer of stainless steel 316L of 25.4 μm (0.001 inches, or 1 mil) thickness. The actual thicknesses of the low impedance layers 140 and 142 of the complex matching layers 136 and 138 of both acoustical transformers 128 and 130 can be determined by running the circuit model 150 to define in the transfer function the theoretical locations of the highest and lowest resonance frequencies of both complex matching layers.

Note that the resonance frequencies 124 and 127 (FIG. 4) of the predicted baseline transfer function 120 (i.e., the highest and lowest predicted resonance frequencies of the acoustical transformers 68 and 92) meet this criteria.

In one embodiment, the thicknesses of the low impedance layers 140 and 142 of the complex matching layers 136 and 138, and/or the thicknesses 86 and 98 of the base matching sections 70 and 94 are altered in a parametric study using the circuit model 150 such that the highest and lowest resonance frequencies are proximate $1.2 \cdot f_C$ and $0.8 \cdot f_C$. Note that resonance frequencies 161 and 162 of the first predicted modified transfer function 160 (i.e., the highest and lowest predicted resonance frequencies) meet this criteria. Accordingly, the predicted resonance frequencies of the acoustical transformers 128 and 130 are all within approximately 20% of the center frequency.

The modeled properties of the acoustical transformers 128 and 130 to obtain the first predicted modified transfer function 160 were as follows:

Transmitting acoustical transformer 128: base matching section 70 of 316L stainless steel with thickness 86 of 0.458λ, complex matching layer 136 including the low impedance layer 140 of polyimide with thickness 88b of 0.2564λ and the protective barrier 132 of stainless steel foil of 0.00445λ thickness.

Receiving acoustical transformer 130: base matching section 94 of 316L stainless steel with thickness 98 of 0.5516λ, complex matching layer 138 including the low impedance layer 142 of polyimide with thickness 104b of 0.151λ and the protective barrier 132 of stainless steel foil of 0.00445λ thickness.

The results show that, for the modified circuit model 150, modeling protective barriers 132 and 134 as 1-mil stainless steel foils (0.00445λ at 1 MHz), adhered to polyimide, the low impedance layer(s) 140 and 142, each of modified thickness to accommodate the thickness of the foil, the first predicted modified transfer function 160 is substantially consistent with the predicted baseline transfer function 120. Even closer matching to the baseline predicted transfer function 120 is possible. Economically, however, a limiting factor is that both KAPTON and stainless steel foils are commercially available only in 1 mil increments. A bandwidth 163 of the frequency response of the first predicted modified transfer function 160, taken as the full width at half the maximum height of the first predicted modified transfer function 160, ranges from about 0.78 MHz to about 1.22 MHz. In practical terms, the bandwidth 163 is the same as the bandwidth of the frequency response of the baseline predicted transfer function 120. Furthermore, the predicted receiver output for the first predicted modified transfer function 160 (y-axis of FIG. 7) is within 70% of the predicted receiver output of the baseline predicted transfer function across the bandwidth 163.

A first actual modified transfer function 164, presented in FIG. 7, was obtained from an acoustical transformer modified in accordance with the protective barriers 132 and 134 of 1-mil foil described above, with the acoustical elements 66 and 90 having center frequencies at 1.0 MHz. The locations of the resonant frequencies of the first actual modified transfer function 164 are in substantial agreement with those of the first predicted modified transfer function 160.

Figure 8:
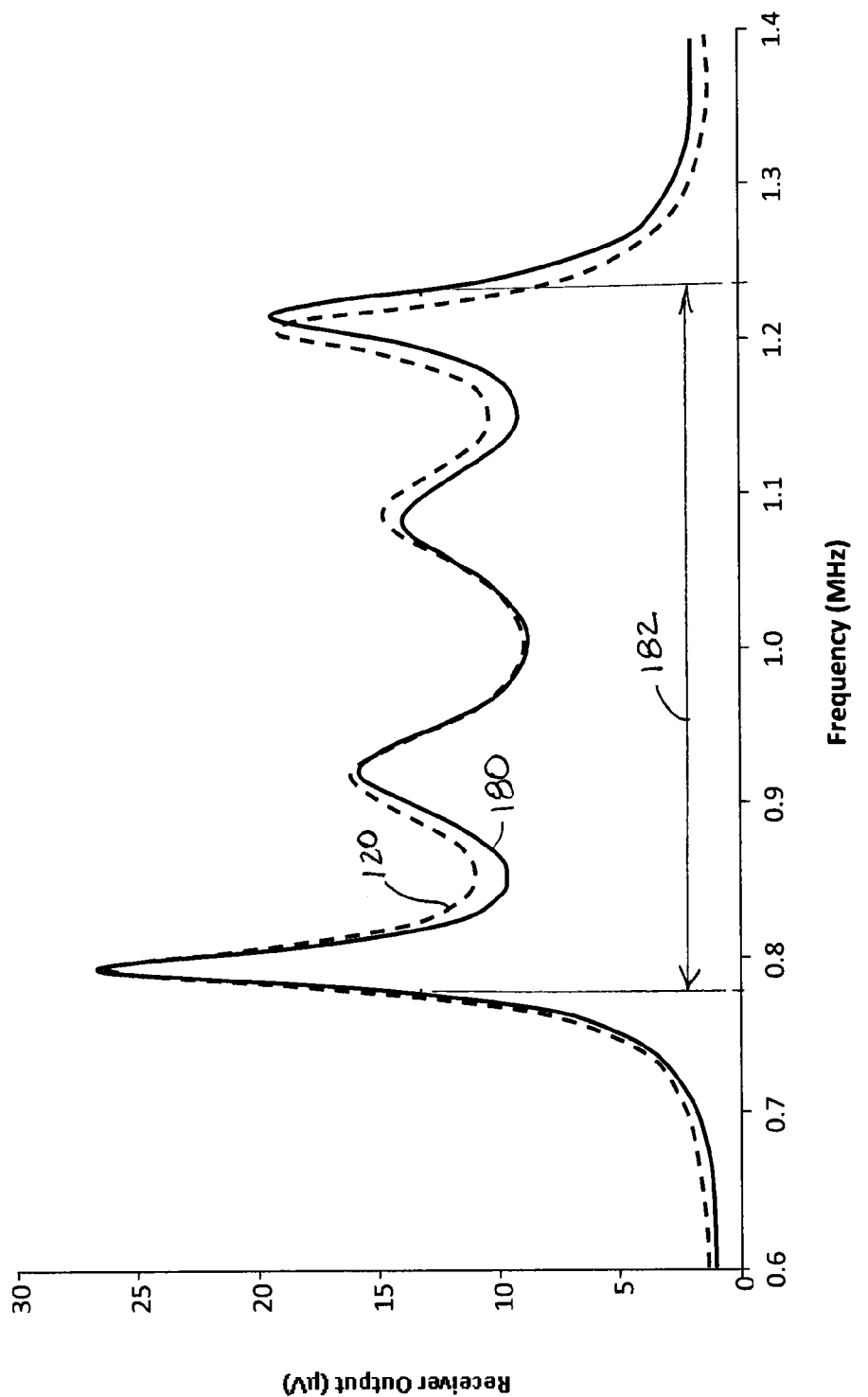
FIG. 8 is a comparison of the predicted baseline transfer function with a predicted second modified transfer function of the modified circuit model of FIG. 6 for a protective barrier of successive layers of gold, nickel and copper bonded to a low impedance layer in an embodiment of the invention.

Referring to FIG. 8, a second predicted modified transfer function 180 from the modified circuit model 150 is compared with the baseline predicted transfer function 120 in an embodiment of the invention. To obtain the second predicted modified transfer function 180, the protective barrier transmission lines 114e and 114f of the modified circuit model 150 was modeled as a composite of successive gold, nickel and copper layers, with the gold being simulated as exposed to the test medium 82, the copper being simulated as deposited directly on the polyimide layer, and the nickel being simulated as interstitial between the gold and copper layers. The actual thicknesses of the low impedance layers 140 and 142 (polyimide) were determined by running the circuit model 150 for definition in the predicted transfer function of the theoretical locations of the highest and lowest resonance frequencies of both complex last matching layers proximate $1.2 \cdot f_C$ and $0.8 \cdot f_C$. Accordingly, the modeled properties of the acoustical transformers 128 and 130 having successive gold, nickel and copper layers for the protective barriers 132 and 134 to obtain the second predicted modified transfer function 180 were as follows:

Transmitting acoustical transformer 128: base matching section 70 of 316L stainless steel with thickness 86 of 0.458λ, complex matching layer 136 including the low impedance layer 140 of polyimide with thickness 88b of 0.291λ thickness and the protective barrier 132 being copper of 0.000638λ thickness, nickel of 0.000451λ thickness and gold of 0.000235λ thickness.

Receiving acoustical transformer 130: base matching section 94 of 316L stainless steel with thickness 98 of 0.5516λ, complex matching layer 138 including the low impedance layer 142 of polyimide with thickness 104b of 0.186λ and the protective barrier 132 being copper of 0.000638λ thickness, nickel of 0.000451λ thickness and gold of 0.000235λ thickness.

The results show that, for the modified circuit model 150, modeling protective barriers 132 and 134 as of successive metallic layers as described above, the modified predicted transfer function 180 is again remarkably consistent with the baseline predicted transfer function 120. A bandwidth 182 of the frequency response of the second predicted modified transfer function 180 is essentially the same as for the baseline predicted transfer function 120 and the first predicted modified transfer function 160 (i.e., from about 0.78 MHz to about 1.23 MHz). Moreover, the predicted receiver output for the second predicted modified transfer function 180 is typically within 90% of the predicted receiver output of the baseline predicted transfer function 120 within the bandwidth 182.

Figure 9:
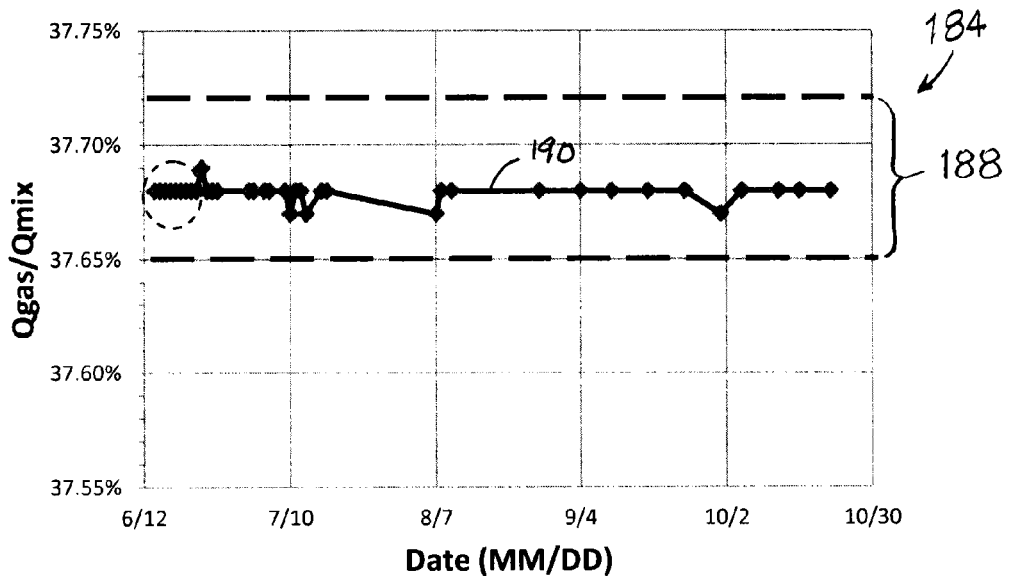
FIG. 9 is a graph of experimental verification test results of an embodiment of the invention exposed to triethylgallium precursor.
Figure 10:
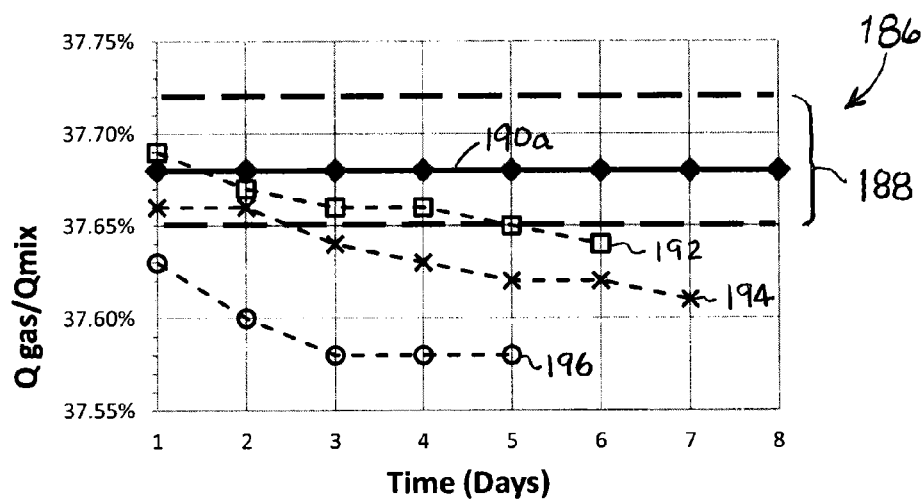
FIG. 10 is a graph of a subset of the experimental verification test results of FIG. 9 along with test results of baseline acoustical sensors exposed to triethylgallium precursor.

Referring to FIGS. 9 and 10, graphs 184 and 186 presenting verification testing results of an embodiment of the invention is depicted. A test procedure, now described, was developed to generate the data presented in graphs 184 and 186.

An unexposed modified Piezocon Sensor, modified to include acoustical transformers 128 and 130 corresponding to those depicted in FIGS. 5A and 5B, was installed in an active MOCVD tool. That is, the modified Piezocon Sensor included a transmitting acoustical transformer 128 having the base matching section 70 of 316L stainless steel, the complex matching layer 136 including a low impedance layer 140 of polyimide (KAPTON) and the protective barrier 132 of stainless steel foil (INCONEL); the receiving acoustical transformer 130 included the base matching section 94 of 316L stainless steel, the complex matching layer 138 including the low impedance layer 142 of polyimide (KAPTON) and the protective barrier 132 of stainless steel (INCONEL) foil.

In addition, three previously unexposed Piezocon Sensors were installed in other active MOCVD tools. Each baseline Piezocon Sensor included acoustical transformers having a construction substantially similar to the baseline acoustical transformers depicted at FIGS. 2A and 2B described above (i.e., having an exposed layer of KAPTON). All of the Piezocon Sensors (modified and baseline) for this experiment were set to measure chlorine concentrations of a chlorine-helium ($Cl_2$—He) mixture while flowing high purity nitrogen ($N_2$) through the Piezocon Sensors. In FIGS. 9 and 10, the concentrations are expressed in terms of a flow ratio Qgas/Qmix, where Qgas is the volumetric flow rate of the gas of interest and Qmix is the volumetric flow rate of the total mixture.

After installation of the various Piezocon Sensors (modified and baseline), the MOCVD tools containing the modified and baseline Piezocon Sensors were operated in a production environment, and exposed to a triethylgallium (TEGa) precursor on a daily basis. TEGa is a substance known to be aggressive in building up oxide layers on exposed KAPTON, which affects performance by decreasing the cavity length. The TEGa can also permeate and swell the KAPTON, causing an increase in thickness and also decreasing the cavity length. The baseline Piezocon Sensors were left in service for a period of several days, while the modified Piezocon Sensors were left in service for a period of several months.

Each day, the respective MOCVD tools would undergo verification procedures where the high purity nitrogen was flowed through the respective Piezocon Sensor. Because of the high purity of the nitrogen flow, the verification procedures provided an opportunity each day to measure the output of the respective Piezocon Sensors while a gas of known molecular weight was passed therethrough. Based on the molecular weight of nitrogen (about 28 g/mole), it was determined that an accurate indication of concentration for the respective Piezocon Sensors set to measure concentrations of $Cl_2$/He (having molecular weights of about 71 g/mole and 2 g/mole, respectively) would be in a range 188 of 37.65% to 37.72%, with fluctuations within 0.01%. The resolutions of the respective Piezocon Sensors were also 0.01%.

Data sets 190 and 190a are presented in both FIGS. 9 and 10, respectively, and represent the data acquired with the modified Piezocon Sensor. The data set 190 illustrates that the modified Piezocon Sensor, with its stainless steel protective barrier, output an indicated concentration of 37.68% that was within ±0.01% over a period of approximately 19 weeks of continuous use.

Meanwhile, data sets 192, 194 and 196, presented in FIG. 10, represent the data acquired with the baseline Piezocon Sensors. Data set 190a, a subset of data set 190, is also presented in FIG. 10 for comparison. All of the baseline Piezocon Sensors demonstrated substantial downward drift over the first few days of exposure to TEGa. Within the first week of operation, the baseline Piezocon Sensor readings all departed significantly below the lower limit (37.65%) of the acceptable range 188. Variations for all of the baseline Piezocon Sensors was on the order of about 0.05% during the first week of operation. Post-experiment analysis revealed a buildup of 10 μm to 12 μm of gallium oxide on the acoustical transformers of the baseline Piezocon Sensors.

The results of graphs 184 and 186 demonstrate both the accuracy and the stability of the modified Piezocon Sensor over the baseline Piezocon Sensors.

The following references, referred to above, are hereby incorporated by reference herein in their entirety except for express definitions and patent claims contained therein: U.S. Pat. Nos. 6,116,080, 6,192,739, 6,199,423 and 6,279,379; Summary of Properties for Kapton® Polyimide Films [.pdf]," available at http://www2.dupont.com/Kapton/en_US/assets/downloads/pdf/summaryofprop.pdf (last visited 24 Aug. 2012); ASTM D-1434-82 (1988).

For purposes of interpreting the claims for the present invention, it is expressly intended that the provisions of Section 112, sixth paragraph of 35 U.S.C. are not to be invoked unless the specific terms "means for" or "step for" are recited in the subject claim.

What is claimed is:

1. An apparatus for acoustically determining a property of a test medium, comprising:
    a chamber for containment of a test medium, said chamber having at least a first side and an inlet for said test medium;
    a first acoustical transformer operatively coupled with the first side of said chamber and configured to at least one of transmit and receive a pulse of acoustical energy with respect to said test medium; and
    an acoustical element operatively coupled with said first acoustical transformer, wherein said first acoustical transformer includes:
a base matching section, a first surface of said base matching section being in contact with said acoustical element;
a last matching section operatively coupled with said base matching section and having an exposed face adapted for contact with said test medium, said last matching section including a protective barrier having a first predetermined thickness disposed on a low impedance layer having a second predetermined thickness to form at least part of said exposed face, wherein the first and second predetermined thicknesses are configured to cooperate to produce a predicted transfer function of the apparatus that is within 70% of a predicted transfer function of an apparatus without a protective barrier, and tailor the resonance frequency of the last matching section such that the highest resonance frequency is limited to below $1.2f_C$ and the lowest resonance frequency is limited to above $0.8f_C$, wherein $f_C$ is the center operating frequency, thereby reducing drift of the first acoustical transformer over time by inhibiting an accrual of a portion of the test medium on the last matching section, while reducing distortion of the at least one of transmitting and receiving of the pulse of acoustical energy caused by the protective barrier.

2. The apparatus of claim 1, wherein said low impedance layer of said first acoustical transformer is in contact with a second surface of said base matching section, said second surface of said base matching section being opposite said first surface of said base matching section.

3. The apparatus of claim 1, wherein said acoustical element is an acoustical transmitter and said first acoustical transformer is configured to transmit said pulse of acoustical energy into said test medium.

4. The apparatus of claim 3, further comprising:
a second acoustical transformer operatively coupled with a second side of said chamber and configured to receive a pulse of acoustical energy transmitted through said test medium; and
an acoustical sensor operatively coupled with said second acoustical transformer,
wherein said second acoustical transformer includes:
a base matching section having a first surface in contact with said acoustical sensor; and
a last matching section operatively coupled with said base matching section of said second acoustical transformer and having an exposed face adapted for contact with said test medium, said last matching section including a protective barrier disposed on a low impedance layer to form at least part of said exposed face.

5. The apparatus of claim 4, wherein said low impedance layer of said second acoustical transformer is disposed on a second surface of said base matching section of said second acoustical transformer, said second surface of said base matching section of said second acoustical transformer being opposite said first surface of said base matching section of said second acoustical transformer.

6. The apparatus of claim 5, wherein said second acoustical transformer is disposed on said second side of said chamber, said second side of said chamber being parallel to said first side of said chamber.

7. The apparatus of claim 1, wherein said metal of said protective barrier is a composite of a plurality of successive metal layers.

8. The apparatus of claim 1, wherein said low impedance layer comprises a polyimide.

9. The apparatus of claim 1, wherein said acoustical element is bi-directional and configured to transmit acoustical energy and receive acoustical energy.

10. The apparatus of claim 1, wherein said test medium is a gas.

11. The apparatus of claim 1, wherein said protective barrier comprises a material that has a carbon dioxide permeability that is less than 700 mL/m²·24 h·MPa over a hypothetical thickness of 25 µm.

12. The apparatus of claim 11, wherein said low impedance layer is polyimide and said protective barrier comprises a fluoropolymer.

13. The apparatus of claim 1, wherein said low impedance layer has a modulus of elasticity that varies less than 50% over a range from 0° C. to 400° C.

14. The apparatus of claim 1, wherein said acoustical element is constructed of a piezoceramic material.

15. The apparatus of claim 1, wherein said protective barrier comprises a metal.

16. A method for constructing apparatus for acoustically determining a property of a test medium, the method comprising:
establishing a predetermined thickness of a protective barrier of a last matching section of an acoustical transformer, said protective barrier being of a low permeability material for exposure to a test medium;
determining a thickness of a base matching section of said acoustical transformer for operative coupling with said last matching section of said acoustical transformer;
determining a thickness of a low impedance layer of said last matching section of said acoustical transformer for contact with said protective barrier, said thickness of said low impedance layer being selected to theoretically provide said acoustical transformer with resonance frequencies that fall within a predetermined frequency range; and
constructing said acoustical transformer having said base matching section and said last matching section, said protective barrier having said predetermined thickness, said low impedance layer having said thickness of said low impedance layer, and said base matching section having said thickness of said base matching section.

17. The method of claim 16, wherein said protective barrier in the step of establishing said predetermined thickness of said protective barrier is metallic.

18. The method of claim 16, wherein said predetermined thickness in the step of establishing said predetermined thickness of said protective barrier is 0.05λ or less, where λ=C/$f_C$, C being the speed of sound in the material of said protective barrier, and $f_C$ being a desired center operating frequency.

19. The method of claim 18, wherein said predetermined thickness of said protective barrier is 0.01λ or less.

20. The method of claim 16, wherein said predetermined frequency range in the step of determining said thickness of said low impedance layer is $0.75·f_C$ to $1.25·f_C$, where $f_C$ is a desired center operating frequency.

21. The method of claim 20, wherein said a lowest predicted resonance frequency is proximate $0.8·f_C$ and a highest predicted resonance frequency is proximate $1.2·f_C$.

22. The method of claim 16, wherein said low impedance layer in the step of determining said thickness of said low impedance layer is polyimide.

23. The method of claim 16, wherein said test medium in the step of establishing said predetermined thickness of said protective barrier is a gas.

24. The method of claim 16, wherein said base matching section in the step of determining said thickness of said base matching section is in physical contact with said last matching section of said acoustical transformer.

25. The method of claim 16, wherein said acoustical transformer is a transmitting acoustical transformer.

26. The method of claim 25, further comprising:
 establishing a predetermined thickness of a protective barrier of a last matching section of a receiving acoustical transformer, said protective barrier of said receiving acoustical transformer being of a low permeability material for exposure to said test medium;
 determining a thickness of a base matching section of said receiving acoustical transformer for operative coupling with said last matching section of said acoustical transformer; and
 determining a thickness of a low impedance layer of said last matching section of said receiving acoustical transformer for contact with said protective barrier of said receiving acoustical transformer,
 wherein said thicknesses of said low impedance layer of said transmitting acoustical transformer and said low impedance layer of said receiving acoustical transformer are selected to theoretically provide both said transmitting acoustical transformer and said receiving acoustical transformers with resonance frequencies that fall within a predetermined frequency range.

27. An apparatus for determining a property of a test medium, the apparatus having an acoustical transformer with a last matching section including a low impedance layer and a protective barrier, said protective barrier being arranged for contact with a test medium, the acoustical transformer being prepared by a process comprising:
 providing a low impedance layer having a first surface and a second surface separated by a predetermined thickness;
 disposing a protective barrier on said second surface of said low impedance layer, said protective barrier being of a predetermined thickness;
 providing a base matching section having a first surface and a second surface separated by a predetermined thickness;
 operatively coupling said first surface of said low impedance layer to said second surface of said base matching section; and
 attaching one of an acoustical sensor and an acoustical driver to said first surface of said base matching section.

\* \* \* \* \*